United States Patent [19]

Christensen et al.

[11] 4,181,733
[45] Jan. 1, 1980

[54] CARBOXYL DERIVATIVES OF THIENAMYCIN

[75] Inventors: Burton G. Christensen, Metuchen; Raymond A. Firestone, Fanwood, both of N.J.

[73] Assignee: Merck & Co., Inc., Rahway, N.J.

[21] Appl. No.: 861,314

[22] Filed: Dec. 16, 1977

Related U.S. Application Data

[63] Continuation-in-part of Ser. No. 733,651, Oct. 18, 1976, abandoned, which is a continuation-in-part of Ser. No. 634,298, Nov. 21, 1975, abandoned.

[51] Int. Cl.² .................... C07D 487/04; A61K 31/40
[52] U.S. Cl. .............................. 424/274; 260/245.2; 546/272; 260/326.31; 424/250; 424/269; 424/270; 424/263; 544/238
[58] Field of Search .................. 260/326.31, 306.8 A, 260/308 D; 424/274, 273, 270, 269; 544/238

[56] References Cited
U.S. PATENT DOCUMENTS 3,950,357   4/1976   Kahan et al. .................. 260/326.31

OTHER PUBLICATIONS
Derwent Abstract 40279y (11-19-76).
Derwent Abstract 34507y (11-16-76).

Primary Examiner—Donald G. Daus
Assistant Examiner—Mary C. Lee
Attorney, Agent, or Firm—Frank M. Mahon; James A. Arno; Julian S. Levitt

[57] ABSTRACT

Disclosed are carboxyl derivatives, i.e., esters, anhydrides and amides, of the antibiotic thienamycin, which has the following structure:

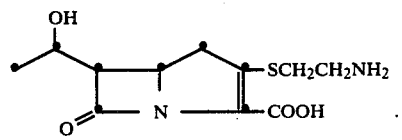

Such derivatives are useful as antibiotics. Also disclosed are processes for the preparation of such derivatives, pharmaceutical compositions comprising such derivatives, and methods of treatment comprising administering such derivatives and compositions when an antibiotic effect is indicated.

5 Claims, No Drawings

CARBOXYL DERIVATIVES OF THIENAMYCIN

BACKGROUND OF THE INVENTION

This is a continuation-in-part of co-pending U.S. Patent application Ser. No. 733,651, filed Oct. 18, 1976, now abandoned which in turn is a continuation-in-part of co-pending U.S. patent application Ser. No. 634,298, filed Nov. 21, 1975, now abandoned.

This invention relates to certain carboxyl derivatives of the new antibiotic thienamycin. Such derivatives (esters, thioesters, anhydrides and amides) are useful as antibiotics. This invention also relates to processes for the preparation of such derivatives, pharmaceutical compositions comprising such derivatives, and methods of treatment comprising administering such derivatives and compositions when an antibiotic effect is indicated.

Thienamycin (I), is disclosed and claimed in co-pending, commonly assigned U.S. patent application Ser. No. 526,992, filed Nov. 25, 1974 (Now U.S. Pat. No. 3,950,357, issued Apr. 13, 1976), which patent is incorporated herein by reference since thienamycin may serve as a starting material for the compounds of the present invention.

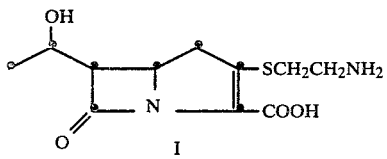

Thienamycin and all of its isomers (in pure form and as mixtures) are also obtainable by the total synthesis disclosed and claimed in co-pending, commonly assigned U.S. patent application Ser. No. 833,210 (15 Sept. 1977). This application is incorporated herein by reference to the extent that it makes available all isomers of I as starting materials in the preparation of the compounds of the present invention.

The thienamycin carboxyl derivatives of the present invention will hereinafter on occasion be referred to as "Th-COXR", for convenience. Also, it is to be noted that the term "carboxy derivatives", i.e., Th-COXR, as defined herein embraces amides, anhydrides, esters and thio esters. The Th-COXR of the present invention may be generically represented by the following structural formula:

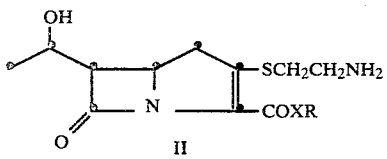

or, more conveniently, by the symbol:

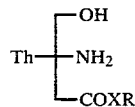

wherein "Th" symbolizes the bicyclic nucleus of thienamycin and the OH, amino and carboxyl groups of thienamycin are illustrated; X is oxygen, sulphur or NR' (R'=H or R); and R is, inter alia, representatively selected from the group consisting of conventional blocking groups such as substituted and unsubstituted benzyl, acyl and the pharmaceutically acceptable salt, ester and amide moieties known in the antibiotic bicyclic β-lactam art; such moieties are given in greater detail below.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of the antibiotic thienamycin but which are characterized as carboxyl derivatives thereof. These antibiotics are active against a broad range of pathogens which representatively include both gram positive bacteria such as *S. aureus, B. subtilis,* and *Strep.pyogenes.* and gram negative bacteria such as *E. coli* and Salmonella. Further objects of this invention are to provide chemical processes for the preparation of such antibiotics and their non-toxic pharmaceutically acceptable salt, ester and amide derivatives; pharmaceutical compositions comprising such antibiotics; and to provide methods of treatment comprising administering such antibiotics and compositions when an antibiotic effect is indicated.

DETAILED DESCRIPTION OF THE INVENTION

In general the compounds of the present invention (II) are prepared by operating upon an N-protected thienamycin species (Ia), followed by N-deblocking to provide II:

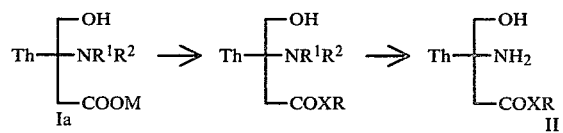

M=H or Metal Cation wherein the symbolism for thienamycin is as defined above and $R^1$ and $R^2$ are independently selected from the group consisting of hydrogen and easily removable N-blocking groups such as acyl blocking groups. Preparation of such N-blocked thienamycin species (Ia) is described below. Usually with respect to Ia, $R^1$ is hydrogen and $R^2$ is acyl or other protecting group; however, direct esterification (I→II) is also possible wherein no protection for N is provided.

In the generic representation of the compounds of the present invention (II, above), the radical represented by —COXR is, inter alia, all radicals known to be effective as pharmaceutically acceptable ester, anhydride (R is acyl) and amide radicals in the bicyclic β-lactam antibiotic art, such as the cephalosporins and penicillins and the nuclear analogues thereof.

Suitable radicals (R) include conventional protecting or carboxyl blocking groups. The term "blocking group" as utilized herein is employed in the same manner and in accordance with the teaching of U.S. Pat. No. 3,697,515, which is incorporated herein by reference. Pharmaceutically acceptable thienamycin derivatives of the present invention falling in this class are given below. Suitable blocking esters thus include those selected from the following list which is representative and not intended to be an exhaustive list of possible ester groups, wherein X=0 and R is given:

(i) $R=CR^aR^bR^c$ wherein at least one of $R^a$, $R^b$ and $R^c$ is an electron-donor, e.g. p-methoxyphenyl, 2,4,6-trimethylphenyl, 9-anthryl, methoxy, $CH_2SCH_3$, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxcarbonyl.

(ii) $R=CR^aR^bR^c$ wherein at least one of $R^a$, $R^b$ and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R=CR^aR^bR^c$ wherein at least two of $R^a$, $R^b$ and $R^c$ are hydrocarbon such as alkyl, e.g. methyl or ethyl, or aryl e.g. phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R=R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula:

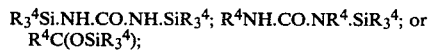

HN(SiR₃⁴)₂ wherein X' is a halogen such as chloro or bromo and the various groups R⁴, which can be the same or different, represent hydrogen atoms or alkyl, e.g., methyl, ethyl, n-propyl, iso-propyl; aryl, e.g. phenyl; or aralkyl, e.g. benzyl, groups.

More generally stated, pharmaceutically acceptable thienamycin carboxyl derivatives of the present invention are those derived by reacting thienamycin (I) or the Ia form with alcohols, phenols, mercaptans, thiophenols, acylating reagents and the like which yield Th-COXR compounds which are bio-labile to conversion to the free acid, I. For example, esters and amides of interest are the compounds of the formula II (above) having the following group at the 2-position: —COXR wherein X is oxygen, sulfur or NR' (R' is as defined above), and R is alkyl having 1-10 carbon atoms, straight or branched, such as methyl, ethyl, t-butyl, pentyl, decyl and the like; carbonylmethyl including phenacyl, p-bromophenacyl, p-t-butylphenacyl, acetoxyacetylmethyl, pivaloxyacetylmethyl, carboxymethyl and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1-10 and preferably 1-6 carbon atoms, but can be branched, staright, or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1-6 carbon atoms and the alkyl portion has 16 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1-6 carbon atoms, e.g., 2,2,2-trichloroethyl, trifluoroethyl, 2-bromopropyl, diiodomethyl, 2-chloroethyl, 2-bromoethyl, and the like; alkenyl having 1-10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1-10 carbon atoms, either straight or branched, e.g., 3-pentynyl, propargyl, ethynyl, 3-butyn-1-yl, and the like; alkanoyl, either straight or branched, having 1-10 carbon atoms, such as pivaloyl, acetyl, propionyl, and the like; aralkyl or heteroaralkyl wherein alkyl has 1-3 carbon atoms, and hetero means 1-4 hetero atoms being selected from the group consisting of O, S, or N, such as benzyl, benzhydryl, and substituted benzyl, benzhydryl, or e.g., benzyl or benzhydryl substituted with 1-3 substituents such as benzyl, phenoxy, halo, loweralkyl, loweralkanoyloxy of 1-5 carbon atoms, lower alkoxy, hydroxy, nitro, blocked carboxy, or combinations thereof, e.g, p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as cycic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1-4 carbon atom chain); or phthalidyl; or phenylethyl, 2-(p-methylphenyl)-ethyl, and the arylthioalkyl analogues, aryloxyalkyl wherein aryl is preferably a phenyl ring having 0-3 substituents, preferably 0 or 1 substituents in the ortho. or para positions and alkyl is 1-6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenoxymethyl, (4-methyl)phenoxymethyl, (2-methoxy)phenoxymethyl, (1-phenoxy)-ethyl, (4-amino)phenoxymethyl, (4-methoxy)phenylthiomethyl, (4-chloro)phenylthiomethyl, phenylthioethyl; aryl wherein aryl is phenyl, 5-indanyl, or substituted phenyl having 0-3 substituents, preferably 0 or 1 substituent in the ortho or para position, e.g., (4-methyl)phenyl, (4- hydroxy)-phenyl, (4-t-butyl)phenyl, p-nitrophenyl, 3,5-dinitrophenyl or p-carboxyphenyl, the latter having either the free acid or the sodium salt form; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)benzyloxymethyl; alkylthioalkyl wherein the alkylthio portion has 1-10 and preferably 1-6 carbon atoms, but can be branched, straight, or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like; alkoxycarbonyloxymethyl, dialkylaminoacetoxymethyl, and alkanoylamidomethyl, wherein the alkyl moieties of the last three mentioned radicals each comprise 1-6 carbon atoms.

In addition to the esters (and thio esters) listed above, amides are also embraced by the present invention, i.e., wherein X is the

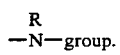

Representative of such amides, Th-CONR'R, are those wherein R' is selected from the group consisting of hydrogen, methyl, ethyl, phenyl, p-methoxyphenyl, benzyl, carboxymethyl, methylthioethyl, and heteroaryl; also embraced by —COXR are anhydrides wherein R is benzyloxycarbonyl, ethoxycarbonyl, benzoyl, and pivaloyl.

Particularly preferred esters are those wherein X is oxygen, sulphur or NR' (R' is hydrogen or lower alkyl having 1-6 carbon atoms) and R is aralkyl, aryloxyalkyl, aralkoxyalkyl, alkylthioalkyl, haloalkyl and alkenyl.

The most preferred compounds of the present invention are those wherein (relative to structure II, above) X is oxygen, and R is selected from the group consisting of: lower alkyl, lower alkenyl, such as methallyl, 3-methylbutenyl, 3-butenyl and the like; methylthio ethyl; benzyl ans substituted benzyl, such as p-t-butylbenzyl, m-phenoxybenzyl, p-pivaloyloxybenzyl, p-nitrobenzyl and the like; pivaloyloxymethyl, 3-phthalidyl, acetoxymethyl, propionyloxymethyl, acetylthiomethyl, pivaloylthiomethyl, allyl, 4-pentenyl, 2-butenyl, 3-methyl-2-butenyl, phenacyl, acetoxyacetylmethyl, pivaloyacetylmethyl, diethylaminoethyl, dimethylaminoethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, acetamidomethyl, The preferred N-blocking groups for the starting material Ia are: carbobenzyloxy, ring-substituted carbobenzyloxy such as o- and p-nitrobcarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as alkylidenes, for example, benzylidene, salicylidene are also of interest.

In general, the N-protected species Ia (above) wherein $R^1$ and $R^2$ are H or acyl are prepared by treating thienamycin (I) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carbocylic acids in the presence of a carbodiimide such as 1,3-dicyclohexylcarbodiimide, and an activated ester of a carboxylic acid such as the p-nitrophenyl esters. The acylation reaction may be conducted at a temperature in the range of from about $-20°$ C. to about $100°$ C. but is preferably conducted at a temperature in the range of from $-8°$ C. to $25°$ C. Any solvent in which the reactants are soluble and substantially inert may be employed, for example, polar solvents such as water, alcohols and polar organic solvents in general such as dimethylformamide (DMF), hexamethyl phosphoramide (HMPA), acetone, dioxane, tetrahydrofuran (THF), acetonitrile, heterocyclic amines such as pyridine, ethylacetate, aqueous mixture of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

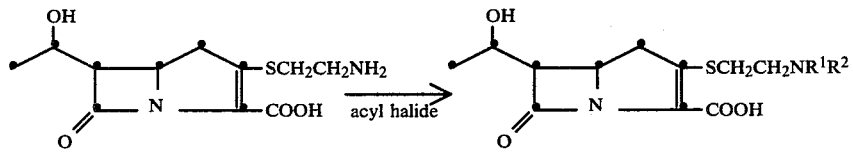

Generally, when the above-described acylating reaction employs an acid halide (suitable halides are chloro, iodo or bromo) or anhydride the reaction is conducted in water or an aqueous mixture of a polar organic solvent such as acetone, dioxane, THF, DMF, acetonitrile or the like in the presence of a suitable acceptor base such as $NaHCO_3$, MgO, NaOH, $K_2HPO_4$ and the like.

Triorganosilyl (or tin) radicals are useful in the preparation of N-blocked thienamycin starting materials. For example, silylation of thienamycin proceeds rapidly to give the tris-triorganosilyl derivative, for example tris-trimethylsilyl (TMS) thienamycin, Th-$(TMS)_3$:

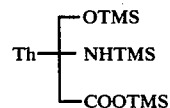

Such derivatives, which are readily soluble in organic solvents, are conveniently prepared by treating Thienamycin with an excess of hexamethyldisilazane and a stoichiometric amount of trimethylchlorosilane at 25° C. with vigorous stirring under a N₂ atmosphere.

The compounds of the present invention II (above) are prepared by conventional procedures known in the art. Such procedures include:

1. Reaction of I or the N-protected free acid (Ia) with a diazoalkane such as diazomethane, phenyldiazomethane, diphenyldiazomethane and the like in an inert solvent such as dioxane, THF, halohydrocarbons, acetonitrile, ethylacetate, and the like at a temperature of from −78° C. to 25° C. for from a few minutes to 2 hours.

2. Reaction of the metallic salts (e.g., Na, Li) of the acid (Ia) with an activated alkyl halide such as methyliodide, benzylbrommide, or m-phenoxybenzylbromide, p-t-butylbenzylbromide, m-phenoxybenzylbromide, and the like. Suitable reaction conditions include inert, anhydrous polar non-protic solvents such as hexamethylphosphoramide, DMF, THF, dioxane, and the like at a temperature of from −78° C. to 25° C. for from a few minutes to 4 hours.

3. Reaction of the free acid (Ia) with an alcohol such as methanol, ethanol, benzyl alcohol, and the like. This reaction may be conducted in the presence of a carbodiimide condensing agent such as dicyclohexylcarbodiimide or the like. Suitable solvents, at a temperature of from 0° C. to reflux for from 15 minutes to 18 hours, include $CHCl_3$, $CH_3CH$, $CH_2Cl_2$ and the like.

4. Reaction of an acid anhydride of Ia, prepared by reacting the free acid (Ia) with an acid chloride such as ethylchloroformate, benzychloroformate and the like, wtih an alcohol such as those listed in 3.) under the same conditions of reaction as given above for 3.). The anhydride is prepared by reaction Ia and the acid chloride in a solvent such as tetrahydrofuran (THF), $CH_2Cl_2$ and the like at a temperature of from 25° C. to reflux for from 15 minutes to 10 hours.

5. Reaction of labile esters of Ia such as the trimethylsilyl ester, dimethyl-t-butylsilyl ester or the like with RX′ wherein X′ is halogen such as bromo and chloro and R is as defined in a solvent such as THF, $CH_2Cl_2$ and the like at a temperature of from 0° C. to reflux for from 15 minutes to 16 hours.

The amides of the present invention are most conveniently prepared by reacting the acid anhydride of Ia with ammonia or with the amine of choice, e.g., the alkyl-, dialkyl-, aralkyl- or heterocyclic amines listed above.

The above-recited schemes of esterification are well-known in the related bicyclic β-lactam antibiotic art and indeed in all of general organic synthesis as and it is to be noted that there is no undue criticality of reaction parameters in the preparation of the compounds of the present invention.

The N-blocking groups, subsequent to the desired esterification reaction of the present invention, may be removed by mild aqueous hydrolysis or by selective hydrogenation or hydrogenolysis. Such deblocking procedures are well known in the art. For purposes of the present invention, suitable conditions for hydrolytic removal of $R^1$ and $R^2$ involve treating the subject thienamycin derivative in dilute aqueous $NaHCO_3$ or the like at a temperature of from about 10° to about 70° C. at a pH of 3–8.5 for from 5 to 70 mins. Typically, removal of the blocking groups by hydrogenation is accomplished in solvents such as ethanol and the like in the presence of a catalyst such as Pt, $PtO_2$ or Pd under 1 to 3 atmosphere of $H_2$ for up to 2 hours at 10° to 40° C.

The compounds of the present invention are valuable antibiotics active against various gram-positive and gram-negative bacteria and, accordingly, find utility in human and verterinary medicine and in inanimate systems. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus.* The antibacterial compounds of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as the active ingredient in any one of a variety of pharmaceutical preparations. These antibiotics and their corresponding pharmaceutically acceptable salt, ester and amide derivatives may be employed in capsule form or as tablets, powders or liquid solutions or as suspensions or elixirs. They may be administered orally, intravenously or intramuscularly. Such pharmaceutically acceptable forms include salts of the free amino group of the compounds of the present invention such as the phosphate, chloride and citrate, as well as salts, esters and amides of appropriate functional groups carrier by the substituent R. Such pharmaceutically acceptable forms are prepared according to procedures well known in the art.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder of liquid sprays or inhalants, lozenges, throat paints, etc. For medication of the eyes or ears, the preparations may be presented as individual capsules, in liquid or semi-solid form, or may be used as drops. Topical applications may be formulated in hydrophobic or hydrophilic bases as ointments, creams, lotions, paints or powders.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms, as for example, in solid or liquid orally ingestible dosage form. The compositions per unit dosage, whether liquid or solid may contain from 0.1 to about 99% of active material, the preferred range being from about 10–60%. The compositions will generally contain from about 15 mg. to about 1500 mg. of the active ingredient; however, in general, it is preferable to employ a dosage amount in the range of from about 250 mg. to 1000 mg. In parenteral administration the unit dosage is usually the pure compounds in a slightly acidified sterile water solution or as the form of a soluble powder intended for solution.

The following examples further illustrate, but do not limit the product, process, compositional or method of treatment aspects of the present invention.

EXAMPLE 1

Preparation of Thienamycin p-tertiary Butylbenzyl Ester

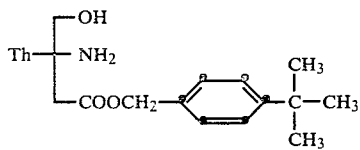

STEP A:

Preparation of N-(p-nitrobenzyloxycarbonyl)Thienamycin Lithium Salt

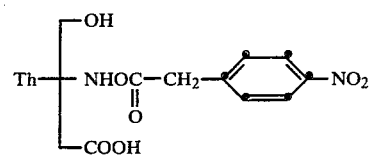

To thienamycin (220 mg.) in 60 ml. water at 0° C. is added successively, 679 mg. $NaHCO_3$, 60 ml. dioxane and then with stirring 1.1 equivalents p-nitrobenzylchloroformate over a period of 1.5 minutes. The mixture is allowed to react 10 minutes, and then is extracted 3× with cold ethyl ether. Electrophoresis (0.05 M, pH 7, phosphate buffer, 50 v/cm, 20 min.) adjusted to pH 2.2 with 1 M $H_3PO_4$ solution and extracted 3× with ethyl acetate.

The ethyl acetate is dried over $MgSO_4$, filtered and reextracted 0.1 N LiOH, to pH 8.2. The final pH is adjusted to 7.0 with 1 M $H_3PO_4$ and the sample is lyophilized. The yield is 205 mg. (54%).

STEP B:

N-(p-nitrobenzyloxycarbonyl)-Thienamycin-p-t-Butylbenzyl Ester

Product of Step A (205 mg.) in 2 ml. hexamethylphosphoramide (HMPA) is treated for 2.5 hrs. with 0.1625 ml. p-t-butylbenzylbromide; the compound is insoluble in HMPA but goes into solution after 30 min.

The reaction mixture is diluted with ethylacetate (EtOAc), washed successively (3×) with water, aqueous $K_2HPO_4$, water, saturated aqueous NaCl, dried over $MgSO_4$, filtered evaporated and subjected to preparative thin layer chromatography on silica gel; eluting with 1:2 $CHCl_3$:EtOAc. Yield 160 mg. (58%), Rf 0.38, IR ($\mu$, film) 2.98 NH and OH 5.63, $\beta$-lactam; 5.86 broad, ester and urethane; NMR ($\delta$, $CDCl_3$), 1.24 (s, $CHCH_3$, t-butyl), 2.59–3.27 (m, $CH_2$) 3.83–4.47 (m, CH $\beta$-lactam), 5.15 (s; $OCH_2C_6H_4NO_2$); 5.22 (s $OCH_2C_6H_4$ t-butyl); 7.45 and 8.12 (AB quartet, J=8 Hz, $C_6H_4NO_2$); 7.33 (s $C_6H_4$-t-butyl).

STEP C:

Thienamycin p-t-Butylbenzyl Ester

The compound of Step B (50 mg.) is dissolved in ethyl alcohol, 35 mg. $PtO_2$ is added and hydrogenated at 50 lbs. pressure for 45 min. The reaction mixture is centrifuged, liquid decanted and evaporated, and subjected to preparative thin layer chromatography on silica gel, eluting with 1:4 methanol: $CHCl_3$, Rf=0.3 yield 28% IR ($\mu$, film) 3.00 ($NH_2$, OH); 5.64 ($\beta$-lactam); 5.90 (ester); NMR ($\delta$ $CDCl_3$) 1.23 (s $CHCH_3$ and t-butyl); 2.65–3.40 (m., $CH_2$); 3.40–4.50 (CH $\beta$-lactam): 5.10 (s $CH_2C_6H_4$); 7.37 (s, $C_6H_4$ t-butyl). M.S. 418, 374, 332, 297, 271, 227, 169, 147, 44.

EXAMPLE 2

Preparation of Thienamycin m-Phenoxybenzyl Ester

Step A:

N-(p-Nitrobenzyloxycarbonyl)-Thienamycin m-phenoxybenzyl Ester

Following the procedure of Example 1, Step B, the title compound is prepared when an equivalent amount of m-phenoxybenzyl bromide is substituted for the p-t-butyl benzyl bromide of Example 1, Step B. Yield 11%, IR ($\mu$, film) 3.0 ($NH_2$, and OH); 5.63 ($\beta$-lactam); 5.86 broad peak (ester and urethane); nmr ($\delta$, $CDCl_3$) 1.33 (d, J=6 Hz $CHCH_3$), 2.60–3.62 (m, $CH_2$) 3.83–4.51 (m, CH $\beta$-lactam); 5.17 (s $OCH_2C_6H_4NO_2$); 5.27 (s, $OCH_2C_6H_4OC_6H_5$); 7.45 and 8.13 (AB quartet J=8 Hz $C_6H_4NO_2$) 7.26 (s, $C_6H_4OC_6H_5$) m.s. 589, 559, 547, 183.

STEP B:

Thienamycin m-Phenoxybenzyl Ester

The title compound is prepared following the procedure of Example 1, Step C, except that the hydrogenation is carried out in ethanol containing a few drops of tetrahydrofuran. IR ($\mu$, film) (3.00, $NH_2$, OH), 5.65 ($\beta$-lactam), 5.91 (ester); nmr ($\delta$, $CDCl_3$); 1.25 (s $CHCH_3$); 2.03–3.79 (m, CH $\beta$-lactam); 5.09 (s $OCH_2 C_6H_4OC_6H_5$); 7.05 (s, $C_6H_4OH_6H_5$); U.V. max 317 nm (hydroxylamine differential curve) m.s. 425, 381, 338, 200, 183.

EXAMPLE 3

Preparation of Thienamycin Benzyl Ester

STEP A:

N-(p-Nitrobenzyloxycarbonyl-Thienamycin Ester

N-((p-Nitrobenzyloxycarbonyl))-Thienamycin (from Example 1, Step A) (205 mg) is treated exactly as described in Example 1, Step B, except that the p-t-butylbenzyl bromide of Example 1, Step B, is substituted by an equivalent amount of benzyl bromide.

STEP B:

Thienamycin Benzyl Ester

Following the procedure of Example 1, Step C, except making the indicated substitution, the title compound is obtained.

EXAMPLE 4

Preparation of Thienamycin-3-Methyl-2-Butene-1-yl Ester

STEP A:

Preparation of N-(p-Nitrobenzyloxycarbonyl)-Thienamycin-3-Methyl-2-butene-1-yl Ester N-(p-Nitrobenzyloxycarbonyl)-Thienamycin sodium salt (11.0 mg., 0.029 mmole) is stirred with HMPA (1 ml.) and 1-bromo-3-methyl-2-butene (39 mg., 0.26 mmole) at 25° C. for 30 min. The mixture is then diluted with 10 ml. ethyl acetate and washed thoroughly with water. The desired product (10 mg.) is isolated by silica gel thin layer chromatography using 1:2 mixture of $CH_3$ and ethylacetate.

STEP B:

Thienamycin-3-Methyl-2-butene-1-yl Ester

Following the hydrogenation procedure of Example 1, Step C, except that an equivalent amount of palladium oxide is substituted for the platinum oxide of Example 1, Step C, the title compound is obtained.

EXAMPLE 5

Preparation of Thienamycin-2-Methylthioethyl Ester

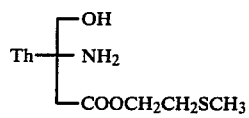

STEP A:

N-(p-Nitrobenzyloxycarbonyl)-Thienamycin-2-Methylthioethyl Ester

Following the procedure of Example 1, Step B, except that the p-t-butylbenzylbromide is substituted by an equivalent amount of 2-methylthio-1-bromo-ethane, the title compound is obtained.

STEP B:

Thienamycin-2-Methylthioethyl Ester

Following the hydrogenation procedure of Example 1, Step C, except for the indicated substitution, the title compound is obtained.

EXAMPLE 6

Preparation of Thienamycin Pivaloyloxymethyl Ester

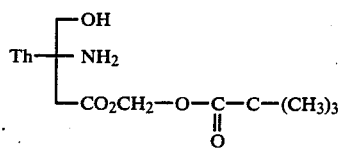

STEP A:

Preparation of N-(p-Nitrobenzyloxycarbonyl)-Thienamycin Pivaloyloxymethyl Ester

N-(p-nitrobenzyloxycarbonyl)-Thienamycin sodium salt (11.0 mg., 0.04 mmole) is stirred with HMPA (1 ml.) and chloromethyl pivalate (36 mg., 0.24 mmole) at 25° C. for 30 min. The mixture is diluted with ethyl acetate and washed with water. The desired product is isolated by TLC using a 1:2 mixture of $CHCl_3$ and ethylacetate.

STEP B:

Thienamycin Pivaloyloxymethyl Ester

Following the hydrogenation procedure of Example 1, Step C, the title compound is prepared when the indicated substitution is made.

13

EXAMPLE 7

Preparation of Thienamycin-2-Methyl-2-propen-1-yl Ester

Step A:

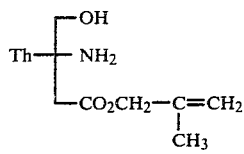

Preparation of N-(p-nitrobenzyloxycarbonyl)-Thienamycin-2-Methyl-2-propen-1-yl Ester N-(p-nitrobenzyloxycarbonyl)-Thienamycin lithium salt (20 mg., 0.055 mmole) is stirred with HMPA (1 ml.) and 3-chloro-2-methylpropene (27 mg. 0.30 mmole) for 30 min. The mixture is diluted with ethyl acetate and washed with water. The desired product is isolated by TLC on silica gel using 1:2 mixture of CHCl$_3$ and ethylacetate.

STEP B:

Thienamycin-2-Methyl-2-propen-1-yl Ester

Following the hydrogenation procedure of Example 1, Step C, the title compound is prepared except that an equivalent amount of palladium oxide is employed rather than the platinum oxide of Example 1, Step C.

EXAMPLE 8

Preparation of Thienamycin Amide

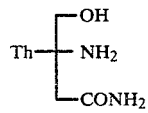

STEP A:

N-Benzyloxycarbonyl-Thienamycin and N-Benzyloxycarbonyl Thienamycin Benzylcarbonic Acid Anhydride A solution of 16.6 mg. of Thienamycin in 4 ml. of 0.05 M pH 7 phsophate buffer and 2 ml. of dioxane in a 3-necked flask fitted with a stirrer, thermometer, pH electrode and the delivery tip of an automatic titrator is cooled to −8° C. in a methanol-ice bath. The pH is brought to 8.2 by the addition of 0.2 N sodium hydroxide in 50% aqueous dioxane and a solution of 0.015 ml of carbobenzyloxy chloride in 2 ml. of chloroform is added. The mixture is stirred at −6° C., pH 8.2, for ten minutes, then layered with ether and the pH adjusted to 7 by the addition of N hydrochloric acid. The layers are separated by centrifugation and the aqueous phase is extracted twice again with ether. The aqueous phase is layered with ethyl acetate and acidified to pH 2. The ethyl acetate is separated and the aqueous layer is extracted again with ethyl acetate. The combined ethyl acetate layer is washed with saturated sodium chloride solution, dried over magnesium sulfate and filtered. The filtrate is stirred with water and the pH brought to 7 by the addition of dilute sodium bicarbonate solution. The aqueous phase is separated and freeze dried giving the sodium salt of N-benzyloxycarbonyl Th. Weight 10 mg. (46%). The UV spectrum, $\lambda_{max}$ 303 m$\mu$, E% 147 ($\epsilon$6,290) indicates about 80% purity. Electrophoresis at 50 V/cm. for 20 minutes at pH 7 followed by bioautograph on *S. aureus* gives a zone of inhibition at +2.5 cm.

The ethereal extracts of the reaction mixture are evaporated and the residue is triturated with hexane which is discarded leaving the desired product N-benzyloxycarbonyl-thienamycin-benzyl carbonic acid anhydride. UV $\lambda_{max}$ 335 m$\mu$. This is hydrolyzed to additional product on standing in 50% dioxane—pH 7 buffer.

STEP B:

N-Benzyloxycarbonyl Thienamycin Amide

A solution of N-benzyloxycarbonyl thienamycin benzyl carbonic anhydride ($\lambda_{max}$ 335 m$\mu$, A=1.41) in 100 ml of ether is slowly titrated with a solution of anhydrous ammonia 0.1 M in ether. The course of the reaction is followed by monotoring the U.V. absorption spectrum at intervals. At the end of the reaction the $\lambda_{max}$ is shifted to 315 m$\mu$ and the absorbence remains constant at 1.06. The solution is concentrated and the N-benzyloxycarbonyl Thienamycin amide is isolated by thin layer chromatography on silica gel using 1:2 mixing of CHCl$_3$ and ethylacetate.

STEP C:

Thienamycin Amide Acetate Salt

A solution of 5 mg of N-benzyloxycarbonyl Thienamycin amide in 1 ml of 95% ethanol containing one equivalent of acetic acid is hydrogenated at 40 psig, and 23° C. in the presence of 5 mg of 5% palladium on charcoal for two hours. The catalyst is removed by filtration and the filtrate is evaporated to a small volume. The product is precipitated by the addition of ether and is recovered by filtration.

EXAMPLE 9

Thienamycin Benzylester from N o-Nitrobenzenesulfenyl Derivative

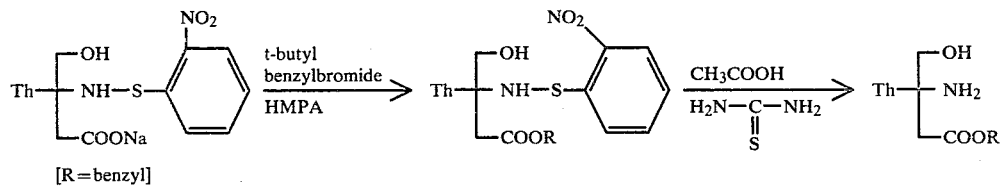

[R=benzyl]

A solution of Thienamycin (100 mg) in 15 ml of 0.05 M pH 7 phosphate buffer and 10 ml of dioxane is cooled to 0°. To this is added with stirring a solution of 100 mg of o-nitrobenzenesulfenylchloride in 5 ml of dioxane during a period of 10 minutes. The pH is maintained at 8.2 during the reaction by the addition of 0.1 N sodium hydroxide under the control of an automatic burette.

The reaction mixture is adjusted to pH 7 and extracted with three 25 ml-portions of ether. The aqueous phase is concentrated and freeze-dried yielding the sodium salt of N-o-nitrobenzenesulfenyl Thienamycin.

A suspension of 30 mg of sodium N- o-nitrobenzenesulfenyl thienamycin in 2 ml of hexamethylphosphoramide (HMPA) containing 50 mg of benzylbromide is stirred at 25° C. for four hours. The mixture is diluted with 20 ml of ethyl acetate and extracted with four 20 ml-portions of 0.1 M pH 7 phosphate buffer then with saturated sodium chloride solution. The ethyl acetate layer is evaporated and the residue purified by chromatography on thin layer silica gel plates to give substantially pure N-o-nitrobenzenesulfenyl thienamycin benzyl ester.

To a solution of N- o-nitrobenzensulfenyl thienamycin benzyl ester (25 ml) in 0.5 ml of dioxane is added 5 mg of thiourea followed by 20 μl of acetic acid. The mixture is kept for 5 minutes at 23° then diluted with 20 ml of ether yielding a precipitate containing thienamycin benzyl ester acetate salt which is recovered by filtration.

EXAMPLE 10

Preparation of Thienamycin p-Isopropylbenzyl Ester

STEP A:

N-(p-Nitrobenzyloxycarbonyl)-Thienamycin-p-Isopropylbenzyl Ester

Following the procedure of Example 1, Step B, except that an equivalent amount of p-isopropylbenzylbromide is substituted for the p-t-butylbenzylbromide of Example 1, Step C, the title compound is obtained.

STEP B:

Thienamycin p-Isopropylbenzyl Ester

Following the hydrogenation procedure of Example 1, Step C, the title compound is obtained when the indicated substitutions are made.

EXAMPLE 11

Preparation of Thienamycin Benzyl Ester

STEP A:

N-(o-Nitrobenzyloxycarbonyl)-Thienamycin Sodium Salt

To Thienamycin (43 mg.) at 0° C. is added 10 ml. 1:1 tetrahydrofuran (THF):Water. The mixture is rapidly stirred while 102 mg. NaHCO3 (10 equivalent) is added, and then, dropwise with stirring over 2 minutes, four equivalents of o-nitrobenzylchloroformate is added. After 30 minutes, the pH is adjusted to 7 with aqueous 25% H3PO4 and the solution extracted 3 X with ether. The aqueous portion is adjusted to pH 2.2 at 0° C.; 500 mg. solid NaCl is added. The cold acidic solution is extracted 3 x with cold EtOAc. The EtOAc extracts are combined and quickly back-washed with cold brine; dried with MgSO4, filtered and back extracted with 10 ml of water containing 1.75 equivalents of solid NaHCO3. The extract is lyophilized in vacuo at 20° C. to provide the title compound.

STEP B:

N-(p-Nitrobenzyloxycarbonyl)-Thienamycin Benzyl Ester

The product of Step A in 7.5 ml. EtOAc is treated with an excess of phenyldiazomethane (4 ml. of a solution comprising 20 mg./ml. ether) at 4° C. for 2 hours. The mixture is concentrated to wet residue at 20° C. under reduced pressure. The desired compound is isolated by thin layer chromatography, eluting with EtOAc; ether (9:1) to afford 17.5 mg. of N-(o-nitrobenzyloxycarbonyl)-thienamycin benzyl ester.

STEP C:

Thienamycin Benzyl Ester

Following the hydrogenation procedure of Example 1, Step C, the title compound is obtained when the indicated substitution is made.

EXAMPLE 12

Preparation of Thienamycin p-Methoxybenzyl Ester

STEP A:

N-(o-Nitrobenzyloxycarbonyl)-Thienamycin p-Methoxybenzyl Ester

To N-(o-Nitrobenzyloxycarbonyl)-thienamycin (70 mg.) in 8 ml. of EtOAc is added 4 ml. of p-methoxyphenyldiazomethane (9 mg/ml acetonitrile) at 4° C. The mixture is stirred for 1.5 hours at 4° C.; whereupon the reaction mixture is concentrated to a wet paste under reduced pressure at 20° C. The title compound (42 mg.) is isolated by thin layer chromatography on silica gel, eluting with EtOAc:ether (9:1).

EXAMPLE 13

Preparation of Thienamycin Methyl and Benzyl Esters via N-(Guanylthioacetamido-thienamycin-Methyl and Benzyl Intermediate Esters

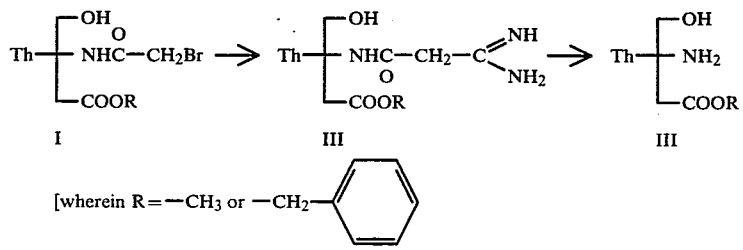

STEP A:

N-Bromoacetyl Thienamycin (I)

To a cooled solution of Thienamycin (28.8 mg.) and sodium bicarbonate (0.3 g.) in 10 ml. of water and 8 ml. of dioxane is added with stirring a solution of 0.25 g. of bromoacetic anhydride in 2 ml. dioxane over a period of 20 minutes. The pH is maintained at 8. The mixture is stirred for an additional 5 minutes then layered with 10 ml. of ether and the pH adjusted to 7 by the addition of 8% phosphoric acid. The ethereal layer is separated and the aqueous layer is extracted twice again with ether. The aqueous layer is evaporated under reduced pressure to 0.5 ml., diluted to 2 ml. with water and put on 50 ml. of XAD-2 resin. The column is eluted with water. The first 80 ml. is discarded, then the next 100 ml. of collected, the solvent is changed to 10% THF and an additional 100 ml. collected. The combined eluates are adjusted to pH 7, evaporated to 5 ml. under reduced pressure, then freeze dried to give the sodium salt of N-bromoacetyl thienamycin in 60% yield. UV $\lambda_{max}$ 302 m$\mu$.

STEP B:

N-Bromoacetyl Thienamycin Methyl and Benzyl Esters

A solution of the sodium salt is layered with ethyl acetate at 0° C. and adjusted to pH 2. The ethyl acetate phase is separated and the aqueous phase is extracted with ethyl acetate. The combined ethyl acetate solutions are dried over MgSO$_4$ and then treated with a solution of diazomethane. The solvents are evaporated and the residue chromatographed on silica gel plate. R$_f$ 0.11 in 2:1 ethyl acetatechloroform. m.p. 118120° C. Mass spectrum shows M$^{30}$ at m/e 406 and significant fragments at m/e 362, 320, 183 and 164.

The corresponding benzyl ester is prepared in a similar way from phenyldiazonemethane. m.p. 142°-3° C. Ir: 5.65$\mu$, 5.89$\mu$ and 6.1$\mu$. Mass spec. m/e 482 (M+), 438, 396, 316, 259 and 164.

STEP C:

N-(Guanylthioacetamido)-Thienamycin Methyl and Benzyl Esters Hydrobromide Salts

A solution of 36 of N-bromoacetyl-Thienamycin methyl ester and 150 mg. of thiourea in 4 ml. of dioxane is kept at 23° C. for 18 hours. The addition of 50 ml of ether gives a precipitate of N-(guanylthioacetamido)-thienamycin methyl ester as the hydrobromide which is recovered by filtration. The corresponding N-(guanylthioacetamido)-thienamycin hydrobromide ester is prepared by following the same procedure except that the benzyl ester of Step B is substituted for the methyl ester.

Step D:

Thienamycin Methyl and Thienamycin Benzyl Esters

A solution of the N-(guanylthioacetamido)-methyl ester hydrobromide salt in 4:1 dioxane-water is adjusted to pH 8 and heated at 37° C. for 1 hour. The solution is evaporated under reduced pressure to the cloud point then extracted with ethyl acetate. The ethyl acetate solution is concentrated and the thienamycin ester isolated by preparative thin layer chromatography on silica gel, using 2:1 mixture of CHCl$_3$ and ethyl acetate.

The corresponding thienamycin benzyl ester is obtained when the N-(guanylthioacetamido)thienamycin benzyl ester hydrobromide of Step C replaces the corresponding methyl ester.

EXAMPLE 14

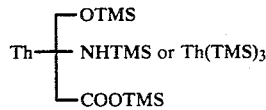

[wherein TMS=trimethylsilyl]

Preparation of Silylated-Th, Th(TMS)$_3$

Antibiotic Th (80.0 mg.) is suspended in 40 ml. THF under a N$_2$ atmosphere and is concentrated to 10 ml. hexamethyldisilazane (1.0 ml.) and trimethylchlorosilane (300 $\mu$l.) is added. The mixture is reacted for 20 minutes at 25° C. with vigorous stirring. The suspension is then centrifuged to remove ammonium chloride. The supernatant is evaporated to an oil under a N$_2$ stream for future reaction.

EXAMPLE 15

Preparation of Thienamycin p-Bromophenacyl Ester

STEP A:

Preparation of N-Bromo-t-Butoxycarbonyl-O-TMS-thienamycin-TMS Ester

Th(TMS)$_3$ (10 mg.) is dissolved in 0.4 ml. of dry tetrahydrofuran to which is added 20 $\mu$l (28 mg., 0.13 mmol) of bromo-t-butylchloroformate (b.p. 35°/0.9 mm) and 8 $\mu$l (5.67 mg., 0.057 mmole) of triethylamine (redistilled from BaO). The mixture is shaken at 25° C., for 20 min. Evaporation of the solvent and excess reagents gives the crude desired product. UV $\lambda_{max}^{EtOAc}$ 320 nm ($\epsilon$ 9,000).

STEP B:

Preparation of O-TMS-N-Bromo-t-Butoxycarbonylthienamycin p-Bromophenacyl Ester

The product of Step A is dissolved in 0.4 ml. of tetrahydrofuran. To this solution is added p-bromophenacyl bromide (9.6 mg., 0.035 mmol) and 20 $\mu$l (14.4 mg., 0.14 mmole) of triethylamine. The mixture is shaken at r.t. for 30 min. and then evaporated to dryness. Ten ml. of ether is added to the residue and the mixture is shaken with 0.2 ml. of 0.1 M pH 7.0 phosphate buffer.

The organic layer is separated, dried over sodium sulfate, concentrated to 0.5 ml. and applied to two 20×20 cm., 250$\mu$ silica gel GF tlc plates which are developed with 30% ethyl acetate in chloroform, (R$_f$=0.68). The desired product (6.7 mg) is isolated in 43% yield.

STEP C:

Thienamycin p-Bromophenacyl Ester

The title compound is obtained when the product of Step B., is treated with ethanol at 40° for 20 minutes and concentrated in vacuo.

EXAMPLE 16

Thienamycin Benzyl Ester

A solution of thienamycin (47 mg) in 1 ml of water and 1 ml of dioxane is cooled to 0° C., and adjusted to pH 5 with N sulfuric acid. Phenyldiazomethane (37.2 mg) in 0.5 ml of dioxane is added during 2 minutes while the pH is maintained at 5 by means of an automatic titrator. After an additional 5 minutes, water (5 ml) is added and the mixture is extracted with ether. The aqueous phase is layered with ethylacetate, cooled and adjusted to pH 2.5. The ethylacetate phase is removed and the aqueous phase is adjusted to pH 8 with sodium bicarbonate and extracted twice with ethylacetate. The ethylacetate extracts are combined, and dried over anhydrous magnesium sulfate. TLC on silica gel in 1:5 methanol chloroform shows a single ninhydrin positive spot at Rf 0.24. The U.V. of the ethylacetate solution shows a λmax at 318 mμ with an optical density of 250.

EXAMPLE 17

Thienamycin Benzhydryl ester

Following the procedure in Example 16 but replacing phenyldiazomethane with diphenyldiazomethane there is obtained thienamycin benzhydryl ester TLC, silica gel, 5:1 CHCl$_3$-MeOH, Rf 0.24.

EXAMPLE 18

Following the procedures set out in the foregoing examples and text, the following compounds of the present invention are obtained:

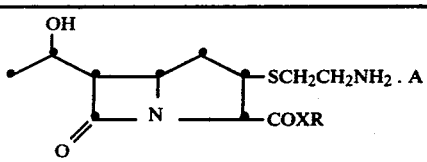

| Compound | X | A | R |
|---|---|---|---|
| 1.) | O | — | CH$_3$ |
| 2.) | O | — | —CH$_2$—⌬—OCH$_3$ |
| 3.) | O | — | —Si(CH$_3$)$_3$ |
| 4.) | O | HCl | —CH$_2$—O—C(=O)—CH$_3$ |
| 5.) | O | HCl | —CH$_2$—O—C(=O)—CH$_2$CH$_3$ |
| 6.) | O | HCl | —CH$_2$—S—C(=O)—CH$_3$ |
| 7.) | O | HBr | —CH$_2$—S—C(=O)—C(CH$_3$)$_3$ |
| 8.) | O | CH$_3$COOH | —CH$_2$—CH=CH$_2$ |
| 9.) | O | CH$_3$COOH | —CH$_2$—CH$_2$—CH=CH$_2$ |
| 10.) | O | HCl | —CH$_2$CH$_2$N—(C$_2$H$_5$)$_2$ |
| 11.) | O | HCl | —CH$_2$—C(=O)—CH$_2$O—C(=O)—CH$_3$ |
| 12.) | O | H$_2$SO$_4$ | —CH$_2$CH$_2$N(CH$_3$)$_2$ |
| 13.) | O | H$_3$PO$_4$ | —CH$_2$—⌬—O—C(=O)—CH$_3$ |
| 14.) | O | — | —CH$_2$—⌬—O—CH(CH$_3$)$_2$ |
| 15.) | O | citric acid | (indanyl group) |
| 16.) | O | tartaric acid | —CH$_2$—O—CH$_2$—⌬ |
| 17.) | O | HCl | —CH$_2$—O—C(=O)—O—CH$_3$ |
| 18.) | O | HCl | —CH$_2$—O—C(=O)—O—C$_2$H$_5$ |
| 19.) | O | CH$_3$COOH | (phthalidyl-type group) |
| 20.) | O | H$_3$PO$_4$ | —CH$_2$—O—C(=O)—CH$_2$—N(C$_2$H$_5$)$_2$ |
| 21.) | O | H$_3$PO$_4$ | CH$_2$—N(H)—C(=O)—CH$_3$ |
| 22.) | S | HCl | —CH$_2$CH$_3$ |
| 23.) | NH | HCl | —CH$_2$—O—CH$_3$ |
| 24.) | O | H$_2$SO$_4$ | —CH$_2$—(pyridyl) |

EXAMPLE 19

Preparation of Pharmaceutical Compositions

One such unit dosage form consists in mixing 120 mg. of thienamycin pivaloyloxymethyl ester with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| Thienamycin Pivaloyloxymethyl Ester | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg) and rough-screened. It is dried at 45° C., and screened again through No. 16 screens. The balance of the cornstarch and the magnesium stearate is added and the mixture is compressed into tablets, approximately 0.5 inch in diameter each weighing 800 mg.

PARENTERAL SOLUTION

Ampoule:
Thienamycin Pivaloyloxymethyl Ester  500 mg.
Diluent: Sterile Water for Injection  2 cc.

OPTHALMIC SOLUTION

Thienamycin Pivaloyloxymethyl Ester  100 mg.
Hydroxypropylmethyl Cellulose  5 mg.
Sterile Water  to 1 ml.

OPTIC SOLUTION

Thienamycin Pivaloyloxymethyl Ester  100 mg.

| | |
|---|---|
| Benzalkonium Chloride | 0.1 mg. |
| Sterile Water | to 1 ml. |
| TOPICAL OINTMENT | |
| Thienamycin Pivaloyloxymtehyl Ester | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients, as for example, with other antibacterial agents such as lincomycin, a penicillin, streptomycin, novobiocin, gentamicin, neomycin, colistin and kanamycin, or with other therapeutic agents such as probenecid.

What is claimed is

1. A compound having the structural formula:

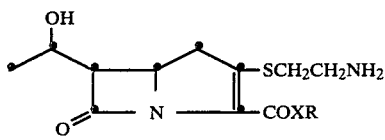

wherein X is oxygen, sulphur or NR' (R'=H or R); R is selected from the group consisting of hydrogen (X is not oxygen); alkyl having 1-10 carbon atoms; phenacyl and nuclear substituted phenacyl wherein the substituent is chloro, bromo, fluoro or alkyl having from 1-6 carbon atoms; alkoxyalkyl wherein the alkoxyl moiety has 1-6 carbon atoms and the alkyl moiety has 1-6 carbon atoms; alkanoyloxyalkyl having 2 to 12 carbon atoms; halo and perhaloalkyl wherein the halo is chloro, bromo, or fluoro and the alkyl chain has 1-6 carbon atoms; alkenyl having from 2-10 carbon atoms; alkoxycarbonyloxyalkyl having 3-14 carbon atoms; dialkylaminoacetoxyalkyl having 4-21 carbon atoms; alkanoylamidoalkyl having 2-13 carbon atoms; benzyl, benzhydryl, p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloxyloxybenzyl, m-pivaloyloxybenzyl, p-isopropoxybenzyl, p-t-butoxybenzyl, 2,2-dimethyl-5-coumaranmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, phthalidyl; phenylethyl, 2-(p-methylphenyl)ethyl, (4-methoxy)phenozymethyl, phenoxymethyl, (4-chloro)-phenoxymethyl, (4-nitro)phenoxymethyl, (4-benzyloxy)methyl, (4-methyl)phenoxymethyl, (4-benzyloxy)-phenoxymethyl, (4-methyl)phenoxymethyl, (2-methoxy)phenoxymethyl, (1-phenoxy)ethyl, (4-amino)phenoxymethyl, (4-methoxy)phenylthiomethyl, (4-chloro)-phenylthiomethyl, phenylthioethyl; (4-methyl)phenyl, (4-hydroxy)phenyl, (4-t-butyl)phenyl; p-nitrophenyl, 3,5-dinitrophenyl or p-carboxyphenyl, the latter having either the free acid or the sodium salt form, 3-phenyl-2-propenyl, benzyloxymethyl, (4-nitro)benzyloxymethyl, (4-chloro)benzyloxymethyl, methylthioethyl, ethylthioethyl, cyclohexylthiomethyl, decylthiobutyl, methylthiopropyl, isopropylthioethyl, methylthiobutyl, phenyl, 5-indanyl, acetylthiomethyl, acetoxymethyl, diethylamino, dimethylaminoethyl, 5-indanylmethyl, p-pivaloylbenzyl, benzyloxymethyl, acetylthioethyl, pivaloylthiomethyl and methylthiomethyl.

2. A compound according to claim 1 wherein R is selected from the group consisting of hydrogen, methyl, t-butyl, phenacyl, p-bromophenacyl; pivaloyloxymethyl, 2,2,2-trichloroethyl, allyl, 3-methyl-2-butenyl, 2-methyl-2-propenyl, benzyl, benzylhydryl, p-t-butylbenzyl, phthalidyl, phenyl, 5-indanyl, acetylthiomethyl, acetoxymethyl, propionyloxymethyl, methallyl, 3-butenyl, 4-pentenyl, 2-butenyl, acetoxyacetylmethyl, pivaloxyacetylmethyl, diethylamino, dimethylaminoethyl, methoxymethyl, p-acetoxybenzyl, p-pivaloylbenzyl, p-isopropoxybenzyl, 5-indanylmethyl, benzyloxymethyl, methylthioethyl, dimethylaminoacetoxymethyl, crotonolacton-3-yl, acetamidomethyl, acetylthioethyl, pivaloylthiomethyl, methylthiomethyl.

3. The compound of claim 1 in which X is oxygen and R is pivaloyloxymethyl.

4. An antibiotic pharmaceutical composition consisting essentially of a therapeutically effective amount of a compound according to claim 1 and a pharmaceutical carrier therefor.

5. An antibiotic pharmaceutical composition consisting essentially of in unitary dosage form, a therapeutically effective amount of a compound according to claim 1 and a pharmaceutical carrier therefor.

* * * * *